United States Patent
Thijs et al.

(10) Patent No.: US 11,395,883 B2
(45) Date of Patent: Jul. 26, 2022

(54) PLUNGER FOR A MEDICAL SYRINGE

(71) Applicants: Datwyler Pharma Packaging International NV, Alken (BE); Hasselt Universiteit, Hasselt (BE)

(72) Inventors: Anita Thijs, Alken (BE); Bram Jongen, Stevoort (BE); Wim Deferme, Hechtel (BE); Inge Verboven, Kortenaken (BE)

(73) Assignees: Datwyler Pharma Packaging International NV, Alken (BE); Hasselt Universiteit, Hasselt (BE)

( * ) Notice: Subject to any disclaimer, the term of this patent is extended or adjusted under 35 U.S.C. 154(b) by 454 days.

(21) Appl. No.: 16/465,612

(22) PCT Filed: Dec. 4, 2017

(86) PCT No.: PCT/EP2017/081326
§ 371 (c)(1),
(2) Date: May 31, 2019

(87) PCT Pub. No.: WO2018/100201
PCT Pub. Date: Jun. 7, 2018

(65) Prior Publication Data
US 2019/0307964 A1    Oct. 10, 2019

(30) Foreign Application Priority Data

Dec. 2, 2016  (DE) ..................... 10 2016 123 302.1

(51) Int. Cl.
*A61M 5/315*    (2006.01)
*A61M 5/31*     (2006.01)

(52) U.S. Cl.
CPC ...... *A61M 5/31513* (2013.01); *A61M 5/3148* (2013.01); *A61M 2205/0238* (2013.01)

(58) Field of Classification Search
CPC ............ A61M 5/31513; A61M 5/3148; A61M 2205/0238
See application file for complete search history.

(56) References Cited

U.S. PATENT DOCUMENTS

2012/0251748 A1* 10/2012 Ashmead .......... A61M 5/31513
                                                    428/34.7
2014/0062036 A1    3/2014 Maeda et al.
(Continued)

FOREIGN PATENT DOCUMENTS

WO   2004/044464 A1   5/2004
WO   2016/039816 A1   3/2016
WO   WO-2016039816 A1 * 3/2016  ........ A61M 5/31578

OTHER PUBLICATIONS

International Search Report of PCT/EP2017/081326, dated Apr. 5, 2018.

*Primary Examiner* — Bhisma Mehta
*Assistant Examiner* — John J Crawford
(74) *Attorney, Agent, or Firm* — Collard & Roe, P.C.

(57) ABSTRACT

A plunger for a medical syringe includes a plunger body having a longitudinal axis, a lateral surface, a front side and a rear side, wherein a first sealing bead is associated with the front side of the plunger, the rear side is used for connecting to a plunger rod and, in addition, a front part of the plunger including the front side is covered with a film-like cover layer for otherwise separating the plunger from the medical substance in the use position. In addition, the cover layer be configured with different thicknesses, wherein the thickness is greatest in the region of the longitudinal axis and decreases radially outwards from the longitudinal axis.

20 Claims, 5 Drawing Sheets

(56) References Cited

U.S. PATENT DOCUMENTS

2014/0319778 A1* 10/2014 Kawasaki ........... A61M 5/3129
　　　　　　　　　　　　　　　　　　　　277/440
2014/0339777 A1　　11/2014 Nakano et al.
2017/0209648 A1*　7/2017 Butts ....................... A61L 31/14

* cited by examiner

PLUNGER FOR A MEDICAL SYRINGE

CROSS REFERENCE TO RELATED APPLICATIONS

This application is the National Stage of PCT/EP2017/081326 filed on Dec. 4, 2017, which claims priority under 35 U.S.C. § 119 of German Application No. 10 2016 123 302.1 filed on Dec. 2, 2016, the disclosures of which are incorporated by reference. The international application under PCT article 21(2) was not published in English.

TECHNICAL FIELD

The invention relates to a plunger for a medical syringe, wherein the plunger comprises a plunger body with a longitudinal axis, with a lateral surface, with a front side and with a rear side, wherein a first sealing bead is associated with the front side of the plunger and the rear side is used for connecting to a plunger rod, wherein in addition a front part of the plunger including the front side is covered with a film-like cover layer for otherwise separating the plunger from the medical substance in the use position.

RELATED ART

Plungers of the kind under discussion are known. They are used in particular in medical syringes to administer or draw fluids to or from a patient, also for example, in the manner preferred in the following, in syringes with a cylindrical body of glass or plastic. A liquid-tight seal is needed between the plunger and the inner wall surface of the cylindrical syringe body. For this purpose, it is known to arrange at least one sealing bead extending circumferentially relative to the longitudinal axis of the plunger. The at least one sealing bead is associated with a front side of the plunger, which faces and is in contact with a medical substance when the substance is administered by means of the syringe.

Such a plunger is known for example from WO 2004/044464 A1. From the same document it is also known to cover the front side of the plunger with a film-like cover layer. This has the effect of separating the plunger material which forms the plunger body from the medical substance inside the syringe barrel.

SUMMARY OF THE INVENTION

In view of the status of the related art as described, the problem to be solved by the invention is to further improve a plunger of the kind under consideration.

According to a first inventive thought, one possible solution to the problem is presented with a plunger in which the decisive feature is that the cover layer is designed with different thicknesses, wherein the thickness is greatest in the region of the longitudinal axis and decreases radially outwards from the longitudinal axis.

The cover layer may be applied with greater material thickness in the central region of the front side of the plunger—which may also be in the form of a tip—than in the radially outer region of the plunger covered by the cover layer. For example, the thickness in the region of the longitudinal axis may be a multiple, for example 2 to 20 times or 5 to 10 times as thick as the smallest thickness of the cover layer in the region radially farthest from the longitudinal axis.

Further features of the invention will be explained in this document, including in the description of the drawing, often in their preferred association with the object of claim 1 or with other features of other claims. However, each such feature may also be significant in an association with only individual features of claim 1 or with only individual features of the respective claim, or independently in each case.

Accordingly, the cover layer may have a smallest thickness from 0.1 to 3 µm.

In a further variant, the cover layer may have a smallest thickness from 0.4 to 1 µm. In a preferred variant, the cover layer has a smallest thickness of 0.5 µm.

The plunger may include one or more sealing beads, each of which extends in a plane perpendicular to the longitudinal axis, a first sealing bead being associated with the front side of the plunger, wherein one sealing bead has a contour which is rounded relative to a longitudinal cross section through the plunger before the plunger is inserted in a syringe, with a largest radial dimension in a plane extending perpendicularly to the longitudinal axis.

When the plunger has been inserted in the syringe and/or the syringe barrel, the region of the largest radial extension of the sealing bead may lie flush against the inner cylinder surface of the syringe. In so doing, the sealing bead may also lose part of its rounded contour in the immediate contact area with the cylinder wall, so that optionally a flat contact area is created between sealing bead and inner cylinder surface. Sections of the sealing bead having cross-sections rounded in this way may be connected by a contact section extending linearly. Thus a cylindrical section may be formed in the region of the largest radial dimension of the plunger, further in the region of the sealing bead, particularly in the region of the sealing bead associated with the front side of the plunger, which cylindrical section extends over ⅒ mm or more up to 2 mm or more in the direction of the longitudinal axis.

In an advantageous variant, the cover layer may extend as far as the radially outermost region of the first sealing bead and in axial direction over 0.1 mm or more up to 3 mm in the direction of the longitudinal axis starting from the point at which it first reaches the outermost region of the first sealing bead.

On a plunger which is under no load and not introduced into the syringe cylinder, the cover layer preferably extends at least as far as the region of the radially largest dimension of the plunger in the region of the sealing bead associated with the front side of the plunger. Thus correspondingly when the plunger is in the set-up position in the syringe cylinder the entire surface of the plunger which comes into contact with the medical substance is covered by the cover layer as far as the sealing zone with the syringe cylinder. The cover layer extends correspondingly preferably to include the sealing zone, wherein the smallest thickness of the cover layer may be reached in said sealing zone. In this way, the cover layer material may advantageously contribute to the further improvement of the plunger's sliding properties along the inner surface of the cylinder wall.

In addition, the cover layer may also extend beyond the largest radial dimension in the region of the sealing bead associated with the front side of the plunger starting from the front side of the plunger.

The thickness of the cover layer may decrease radially outwardly either continuously or in steps. If the decrease is in steps, not only may a sharp decrease in the thickness of the cover layer material be realised, but rather a continuous decrease in thickness realised in this step region as well, which however has a greater decrease in thickness over a radial extension dimension when viewed in the cross-section of the plunger than in the cover layer region before and after the step in a radial extension dimension viewed in the same way. Additionally, starting from the region of greatest thickness the thickness of the cover layer may initially remain constant with increasing radial distance, and may not decrease until closer to the radially outer region.

The smallest thickness of the cover layer may be associated with the radially outermost region of the plunger in the region of the first sealing bead. Beyond this radially outermost region—viewed starting from the front side of the plunger—the cover layer, if present, may also be designed to have greater thickness, alternatively it may be constantly of the smallest thickness or it may even decrease to nothing.

A radial dimension of the cover layer, starting from a radial dimension which is realised the first time the thickness becomes less than 3 times the smallest thickness, may be equivalent to one fifth or less, for example one sixth or one tenth up to as much as one twentieth of the largest radial dimension.

The cover layer may be applied to the plunger in a spraying process. This spraying process is preferably carried after the plunger body is produced, preferably from a rubber material.

The cover layer may also be designed as a separate part which is applied to the plunger. In such case, it may be a prefabricated film, which in a preferred variant has a material thickness which becomes smaller outwards from the inside.

The application of the film-like cover layer to the plunger may be achieved as the result of a fusion process. In addition, the entire production of the plunger with the film-like cover layer in the in-mould-labelling process is also possible.

Production of the plunger furnished with the cover layer in a two-component spraying process is also possible.

The cover layer may have one or more protrusions on the side thereof closest to the plunger, which are designed for form-fitting engagement in corresponding recesses in the front side of the plunger. This makes it possible to obtain a correctly aligned attachment of the cover layer, particularly if it has been manufactured as a separate part. The recess on the plunger side is preferably designed to engage in form-fitting manner with the protrusion on the cover layer.

In this way, a protrusion and an associated recess may be arranged symmetrically with respect to a longitudinal cross section through the plunger, or the longitudinal axis may pass through them. In this context, a concentric arrangement of recess and protrusion with respect to the longitudinal axis of the plunger is preferred.

The plunger may have a sealing layer of constant thickness over its entire lateral surface, except as far as the region of the first sealing bead. In corresponding manner, when viewed from the front side of the plunger, after reaching the first largest radial extension in the region of the first sealing bead, the cover layer thickness may be constant as far as the rear side of the plunger.

The constant thickness which may be provided in the region of the entire lateral surface, may have a dimension from 0.3 to 3 µm, preferably for example 0.4 to 1 µm, particularly 0.5 µm. Moreover, the constant thickness may match the smallest cover layer thickness in the region of the entire lateral surface.

In a preferred variant, the thinnest region of the cover layer is selected to be dimensionally smaller than corresponding to the peak-to-valley height of the plunger material. When the cover layer is applied in the spray process, a roof-like canopy of the valleys that arise as a result of the roughness may form in the plunger surface.

In the form of a separate, film-like part that is to be applied, the cover layer may consist of a fluorine-based plastic material, for example a fluorine-containing (co-) polymer, preferably for example ethylene tetrafluoroethylene (ETFE), perfluoroethylene propylene copolymer (FEP), a terpolymer of tetrafluoroethylene, hexafluoropropylene and vinylidene fluoride (THV), polyvinyl fluoride (PVF), perfluoroalkoxy polymer (PFA), injection-mouldable polytetrafluoroethylene (PTFE), polychlorotrifluoroethylene (PCTFE), ethylene chlorotrifluoroethylene (ECTFE) or polyvinylidene fluoride (PVDF).

The ranges and value ranges or multiple ranges stated in the preceding and the following text also include all intermediate values for the purposes of the disclosure, in particular in increments of ¹/₁₀ of the respective dimension, thus also without specification of a dimension where applicable. For example, the specification 0.3 to 3 µm also includes the disclosure of 0.4 to 3 µm, 0.3 to 2.9 µm, 0.4 to 2.9 µm, etc. This disclosure may serve to define an identified upper and/or lower range limit, and alternatively or additionally thereto also to disclose one or more singular values from a respective given range.

BRIEF DESCRIPTION OF THE DRAWING

In the following text, the invention is explained with reference to the accompanying drawing, which however only represents exemplary embodiments. A part which is explained only with reference to one of the exemplary embodiment and which is not replaced in another embodiment due to the particular property revealed there, is thus included as a part which is at any rate possibly present for this other embodiment as well. In the drawing.

DESCRIPTION OF THE EMBODIMENTS

Figure 1:
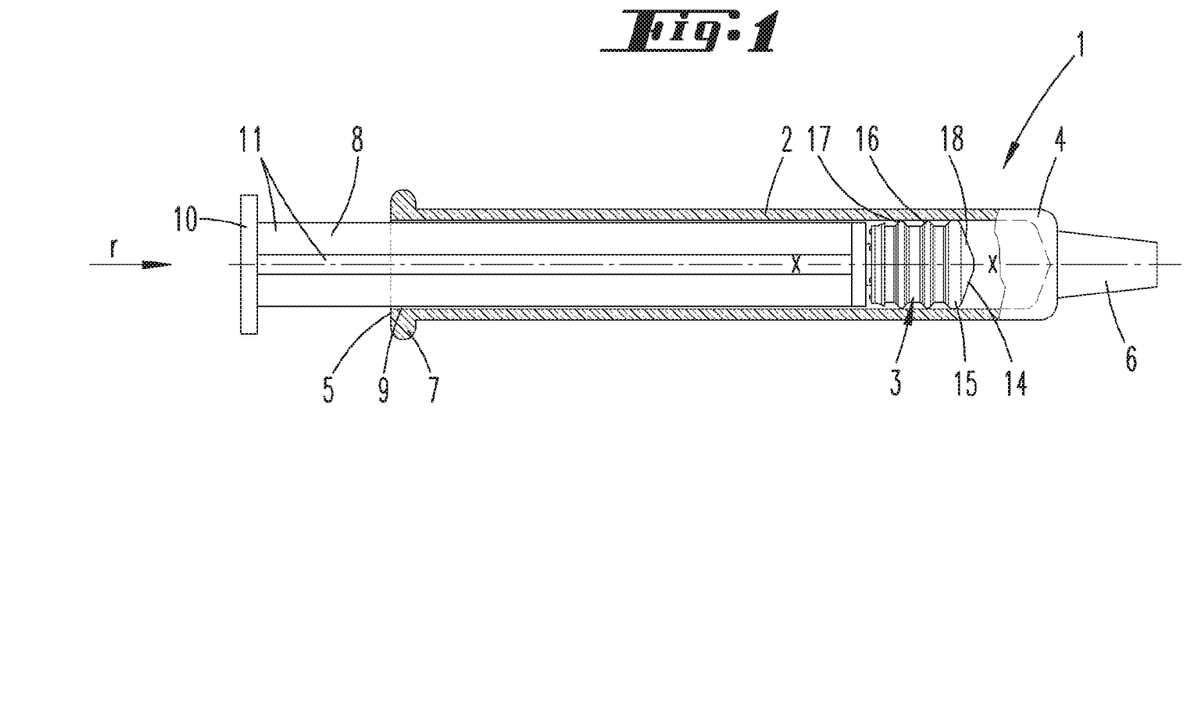
FIG. 1 is a partial sectional view of a medical syringe with a plunger.
Figure 2:
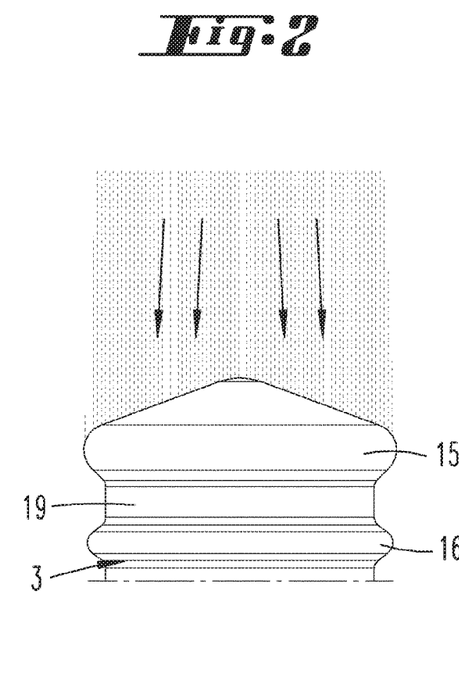
FIG. 2 shows a first embodiment of a plunger during a spraying process for applying a cover layer.

Firstly with reference to FIG. 1, a syringe 1 for medical purposes is represented and described.

The syringe 1 is composed essentially of an elongated cylinder 2 which is open at both ends, particularly a cylindrical body made for example of glass or plastic, and a plunger 3 which is displaceable inside the cylinder 2 in a direction of advance r and in a direction opposite to the direction of advance r.

The cylinder 2 has a distal end 4 and a proximal end 5. In the region of the distal end 4 the cylinder 2 adjoins a tapered needle hub 6.

A radial enlargement in the form of a flange 7 is conformed in the region of the proximal end 5. During use of the syringe 1, this serves as a counterholder enabling support under the flange for preferably the index and middle fingers of the hand operating the syringe 1.

The plunger 3 is connected to a plunger rod 8. The plunger rod passes through an insertion opening 9 of the cylinder 2 provided in the proximal end 5 and forms a plate-like thumbrest 10 aligned transversely to the lengthwise extension of the plunger rod 8 in the region of the free end 2 farthest from the plunger 3.

As represented, the plunger rod 8 may have the form of fins 11 aligned in cross-like manner.

The plunger of the embodiments represented is preferably produced from a rubber material.

The plunger 3 further has a longitudinal axis x which is coincident with the longitudinal axis of the cylinder 2 of the syringe 1 in the use position according to FIG. 1.

A receiving opening 12 with an internal thread 13 for screwed fastening of the facing distal end of the plunger rod 8 is formed on the plunger 3 coaxially with longitudinal axis x and accessible from the rear end relative to the direction of advance x.

The plunger 3 is furnished with a tip section 14 in the region of the front side of the plunger 3 which faces the distal end 4 of the cylinder 2 in the region of the front side of the plunger 3 in the use position. As shown in the exemplary embodiments, this tip section may be conical in shape. With the tip section 14 as shown, fluid can be expressed completely from the interior of the cylinder 2 through the needle hub 6 which is arranged coaxially with the longitudinal axis x in the region of the distal end 4.

The plunger 3 is furnished with at least one sealing bead 15 extending circumferentially relative to the longitudinal axis x. In the exemplary embodiments shown, three such sealing beads 15 to 17 are provided preferably at equal distances from each other in the direction of extension of the longitudinal axis x.

Figure 3:
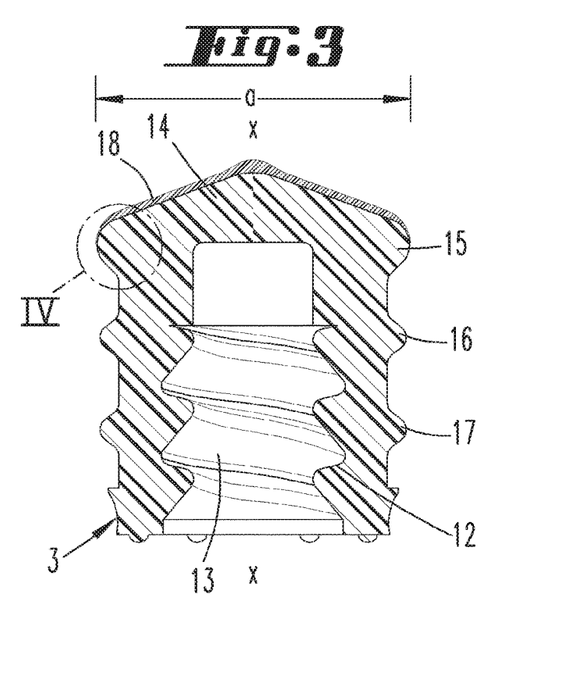
FIG. 3 shows a full cross-section of the plunger of FIG. 3 furnished with the cover layer.
Figure 4:
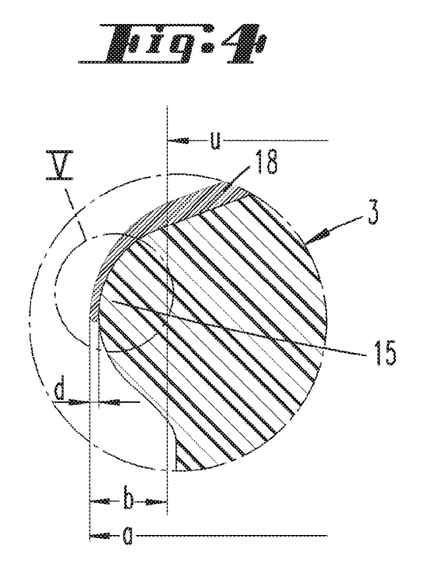
FIG. 4 shows the enlarged view of inset IV in FIG. 3.
Figure 5:
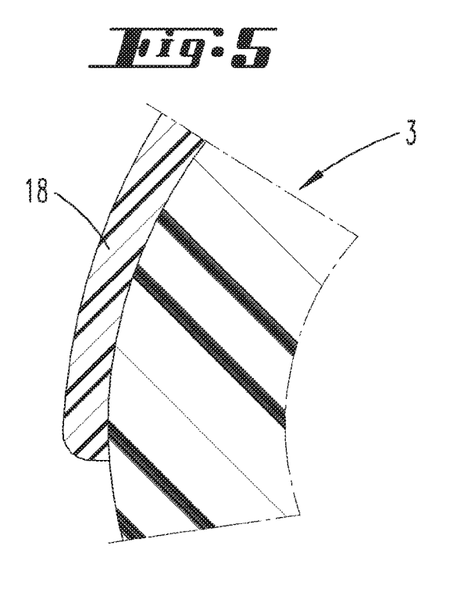
FIG. 5 shows a macroscopic enlargement of region V in FIG. 4.

In this context, the sealing bead 15 is associated with the front side of the plunger 3 and in a preferred variant directly adjoins the tip section 14, so that the transition of surface of the tip section 14 in a roof-like formation in the cross-section of FIG. 3 to the surface of the sealing bead 15 is preferably smooth.

The cross-section(s) of the sealing bead(s) 15 and optionally 16 and 17 are of rounded construction, particularly before the plunger 3 is inserted in the cylinder 2. In this way, sealing zones are formed by correspondingly ring-like beads and connected to each other via preferably completely cylindrical plunger sections.

The sealing beads 15 to 17 serve to provide liquid-tight support of the plungers 3 against the inner wall of the cylinder.

Each sealing bead, but particularly the sealing bead 15 has a largest radial dimension a in a plane extending perpendicularly to the longitudinal axis x, which largest radial dimension a is formed at the apex of the rounded sealing bead 5 in the unmodified plunger 3, i.e. when the plunger 3 is not inserted in the cylinder 2.

The plunger 3 is covered by a cover layer 18 in the region of its front side. This may be a layer which seals the surface of the plunger 3 facing the medical substance when the syringe 1 is used, so that no direct contact takes place between the actual plunger material and the medical substance.

As may be seen in the illustrations, the cover layer 18 extends radially outwardly relative to a cross section, starting from a central tip region of the plunger 3 through which the longitudinal axis x passes until the largest radial dimension a is reached in the region of the first sealing bead 15, as shown in FIG. 3 for example.

Figure 7:
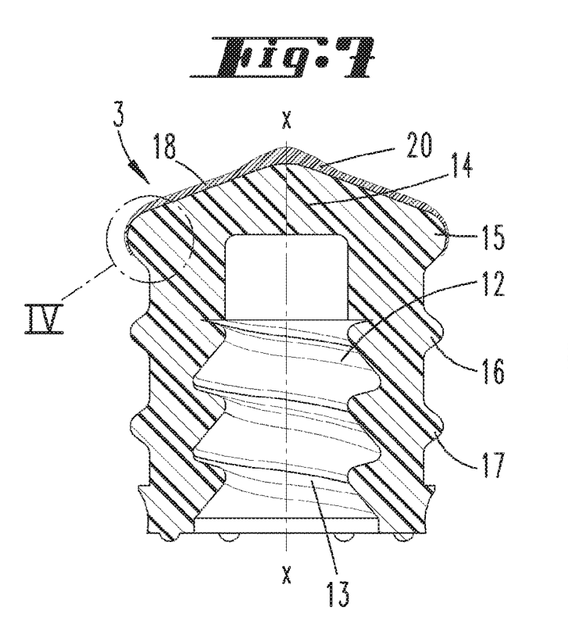
FIG. 7 is a representation corresponding to FIG. 3 relating to the embodiment of FIG. 6.
Figure 8:
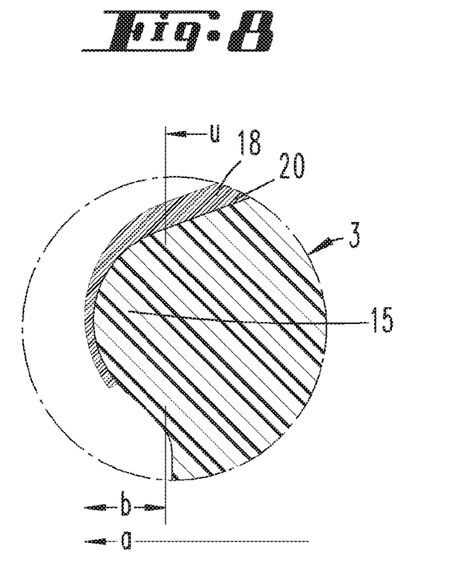
FIG. 8 shows the enlarged view of inset VIII in FIG. 7.

According to the embodiment of FIG. 7, the cover layer 18 may extend over a dimension of 2 µm or more up to 3 mm or more beyond the radial dimension a in the region of the sealing bead 15 starting from the front side of the plunger 3, originating from the plane of the largest radial dimension a in the direction of extension of the longitudinal axis x. The figure shows an embodiment in which the cover layer 18 extends as far as the rear side of the first sealing bead 15 farthest from the front side of the plunger 3, and in this case does not extend as far as the following cylindrical section of the plunger 3.

Figure 9:
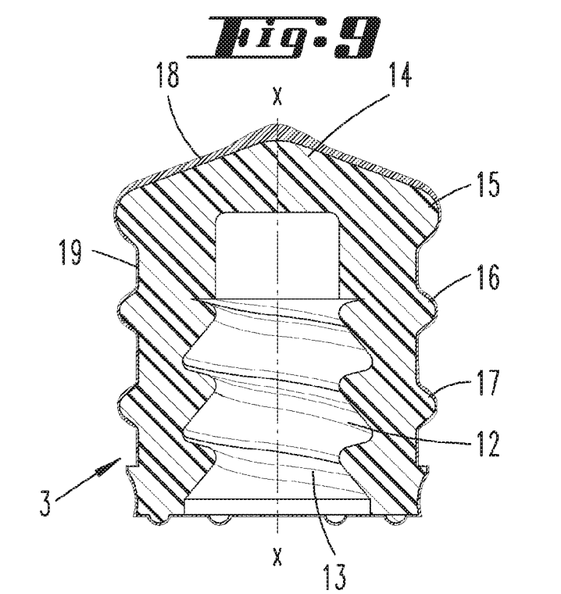
FIG. 9 is a representation corresponding to FIG. 3 relating to a further embodiment.

As represented in FIG. 9, the cover layer 18 may also be provided to completely cover the lateral surface 19 of the plunger 3. In this case, the cover layer extends over the tip section 14 and along the sides of the plunger 3 over all sealing beads 15 to 17 and the cylindrical sections of the plunger 3 that connect them as far as the rear and of the plunger 3.

As may further be seen in the illustration, the thickness d of the cover layer 18 is provided which decreases radially outwardly starting from the region through which the longitudinal axis x passes. The decrease in thickness radially outwards from the inside may be provided in continuous fashion, as shown.

The smallest thickness of the cover layer 18 may be provided in the region of the largest radial dimension a, i.e. preferably in the apex region of the sealing bead 15 associated with the front side of the plunger 3. The smallest thickness d of the cover layer 18 may have a dimension of 0.5 µm. for example.

In this way, a cover layer 18 may be created in which a radial dimension b of the cover layer 18 starting from the radial dimension u corresponds to one fifth or less of the largest radial dimension a, wherein the radial dimension u is present the first time the thickness becomes less than three times greater then the smallest thickness d of the cover layer 18 (see FIG. 3).

The cover layer 18 may be applied to the front side of the plunger by spraying (see also FIGS. 2 to 5).

In this context, a decrease in the cover layer thickness d is realised particularly in the curved section of the sealing bead 15, further in the region of the largest radial dimension a.

In this context, the smallest thickness of the cover layer has a dimension which is preferably selected smaller than the peak-to-valley height of the plunger material.

Figure 6:
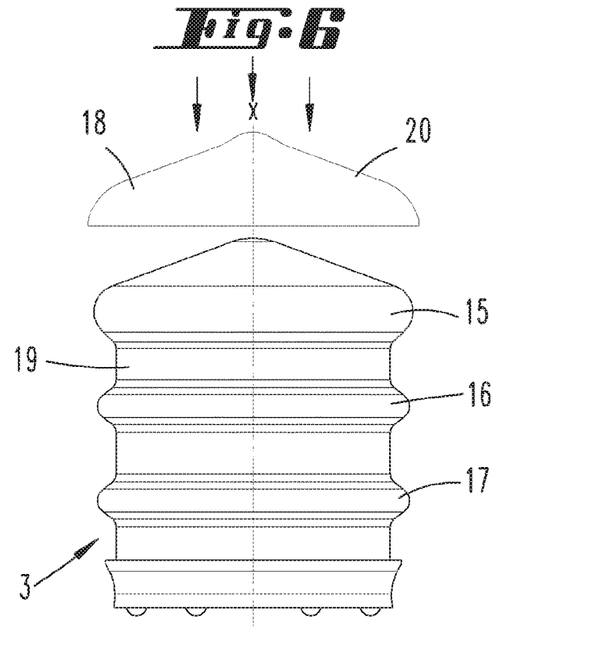
FIG. 6 is a representation similar to FIG. 2 relating to a second embodiment during application of the cover layer as separate films.

The cover layer 18 may also be embodied as a separate part 20, in particular as a film part (see FIG. 6). This separate part is applied separately to the front side of the plunger 3 and bonded thereto or alternatively joined to the plunger material in the course of the production process of the plunger 3, in an in-mould process for example.

In the course of the associated production process, the film-like cover layer 18 may be furnished with a thickness which decreases radially outwardly until a smallest thickness is reached in the preferably radially outermost region.

Upon reaching the preferably predefined smallest thickness, the layer material extends further, maintaining smallest thickness.

Figure 10:
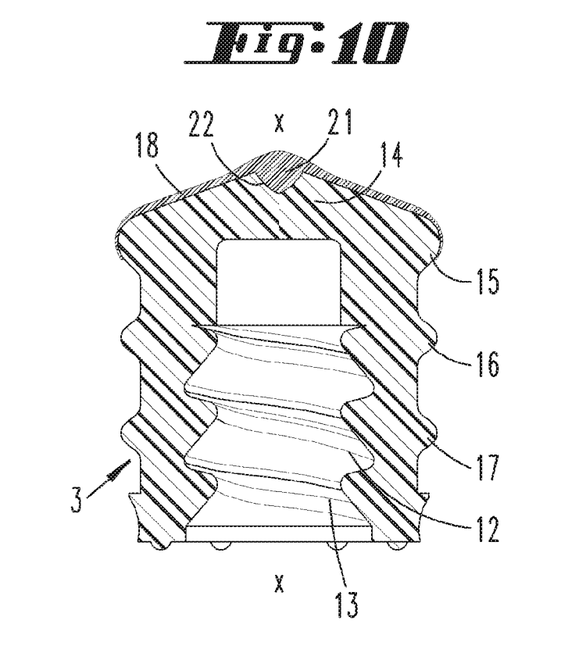
FIG. 10 shows the plunger in a further embodiment in a representation similar to that of FIG. 3.

Particularly such a separately produced part 20 may be furnished for the purpose of exact alignment with the plunger 3 with a protrusion 21 facing towards the plunger 3, which protrusion is insertable in an associated recess 22 in the plunger 3, for example in the region of the tip section 14 thereof for a form-fitting connection (see FIG. 10).

A combination of spraying on a cover layer and applying a separately produced cover layer may be provided, such as further for example in a possible variant of the plunger 3 according to the representation in FIG. 9, in which the circumferential plunger shell is also furnished with a cover layer 18. This cover layer may be sprayed on with uniform thickness, in such case in the region of the tip section 14 on the plunger side, further optionally covering said tip section completely. Finally, a cover layer film having a thickness that decreases radially outwardly may be applied to the tip section 14, correspondingly on the front side of the plunger 3.

The material of the cover layers 18 for covering the lateral surface 19 of the plunger may optionally be the same as or different from the cover layer material of the tip section 14.

Figure 11:
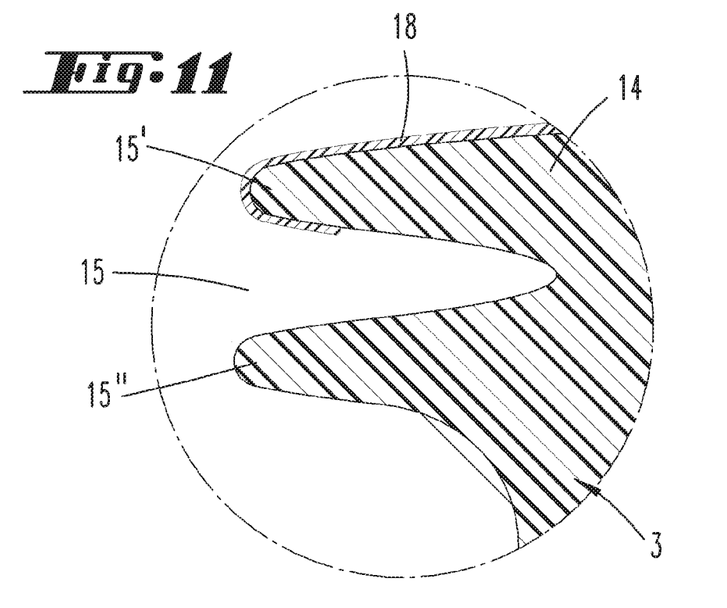
FIG. 11 is an enlarged view of a further embodiment corresponding to FIG. 4.
Figure 12:
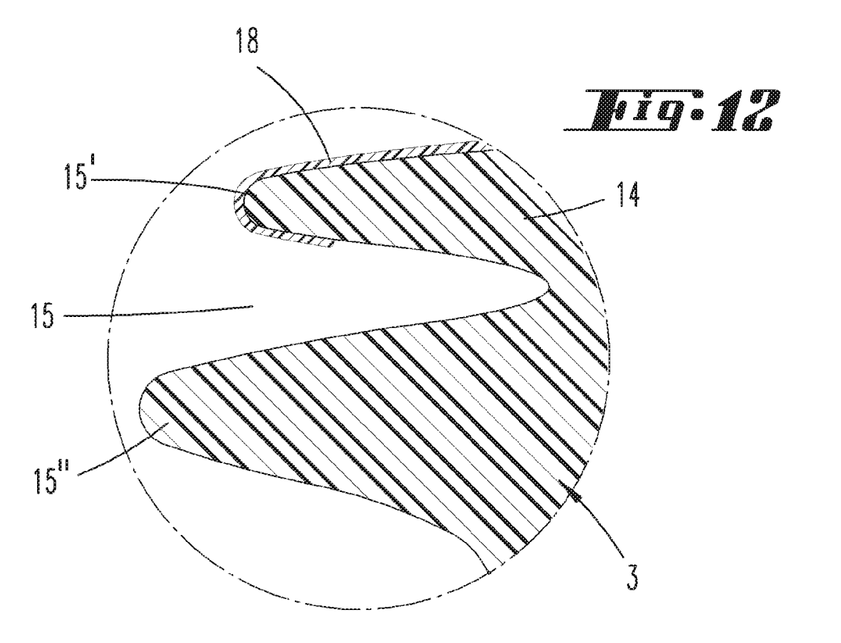
FIG. 12 is a representation of a further embodiment corresponding to FIG. 4.

As shown in the enlarged insets in FIGS. 11 and 12, the sealing bead 15 may also be embodied as a double bead with two immediately sealing zones located immediately one after the other in the axial direction, wherein the sealing zones 15' and 15" may have the same diameter. Alternatively, the diameter of the sealing zone 15" farthest from the tip region may selected larger than the closer sealing zone 15'. In this case, the cover layer 18 of the tip section 14 preferably only extends behind the first sealing zone 15' of the sealing bead 15. The second sealing zone 15" may cooperate directly with the facing interior surface of the cylinder 2 without a cover layer, as is preferred.

The preceding notes serve to explain the totality of the inventions included in the application which advance the related art also individually, at least by the following combinations of features, specifically:

A plunger 3 which is characterized in that the cover layer 18 is constructed with various thicknesses, wherein the thickness d is largest in the region of the longitudinal axis x and decreased radially outwardly starting from the longitudinal axis x.

A plunger 3 which is characterized in that the cover layer 18 has a smallest thickness d from 0.1 to 3 µm.

A plunger 3 which is characterized in that the cover layer 18 has a smallest thickness d from 0.4 to 1 µm.

A plunger 3 which is characterized in that the cover layer 18 has a smallest thickness d of 0.5 µm.

A plunger 3 which is characterized in that the plunger 3 is furnished with one more sealing beads 15-17 extending in a plane perpendicularly to the longitudinal axis x, which a first sealing bead 15 associated with the front side of the plunger 3, wherein one sealing bead 15-17 has a contour which is rounded relative to a longitudinal cross section through the plunger 3 before the plunger 3 is inserted in a syringe, with a largest radial dimension a in a plane extending perpendicularly to the longitudinal axis x.

A plunger 3 which is characterized in that the cover layer 18 extends as far as the radially outermost region of the first sealing bead 15 and in axial direction over 0.1 mm or more up to 3 mm in the direction of the longitudinal axis x starting from the point at which it first reaches the outermost region of the first sealing bead 15.

A plunger 3 which is characterized in that the thickness of the cover layer 18 decreases radially outwardly continuously or in steps.

A plunger 3 which is characterized in that the smallest thickness d of the cover layer 18 is associated with the radially outermost region of the plunger 3 in the region of the first sealing bead 15.

A plunger 3 which is characterized in that a radial dimension a of the cover layer 18 starting from a radial dimension u which is realised the first time the thickness becomes less than 3 times the smallest thickness d, is equivalent to one fifth or less of the largest radial dimension.

A plunger 3 which is characterized in that the cover layer 18 is applied to the plunger 3 in a spray process.

A plunger 3 which is characterized in that the cover layer 18 is designed as a separate part 20 and applied to the plunger 3.

A plunger 3 which is characterized in that the cover layer 18 has one or more protrusions 21 on the side thereof facing the plunger 3 for a form-fitting engagement in corresponding recesses 22 in the front side of the plunger 3.

A plunger 3 which is characterized in that a protrusion 21 and an associated recess 22 are arranged symmetrically with respect to a longitudinal cross section through the plunger 3, or the longitudinal axis x bisects them symmetrically.

A plunger 3 which is characterized in that the plunger 3 has a cover layer 18 of constant thickness d over its entire lateral surface 19, except as far as the region of the first sealing bead 15.

A plunger 3 which is characterized in that the constant thickness d has a dimension up to 3 µm.

All disclosed features are essential to the invention individually but also in combination with each other. The disclosed content of the associated/accompanying priority documents (photocopy of the preliminary application) is herewith also included in its entirety in the disclosure of the present application also for the purpose of incorporating features of those documents in the claims of the present application. The features described in the subclaims characterize independent inventive further developments of the related art, particularly to enable partial applications to be made on the basis of these claims.

REFERENCE LIST

1 Syringe
2 Cylinder
3 Plunger
4 Distal end
5 Proximal end
6 Needle hub
7 Flange
8 Plunger rod
9 Insertion opening
10 Thumbrest
11 Fin
12 Receiving opening
13 Internal thread
14 Tip section
15 Sealing bead
15' Sealing zone
15" Sealing zone
16 Sealing bead
17 Sealing bead
18 Cover layer
19 Lateral surface
20 Part 21 Protrusion
22 Recess
a Radial dimension
b Radial dimension
d Thickness
r Direction of advance
u Radial dimension
x Longitudinal axis

The invention claimed is:

1. A plunger (3) for a medical syringe (1), wherein the plunger (3) has a plunger body with a longitudinal axis (x), a lateral surface, a front side, a rear side, and a plurality of sealing beads, wherein a first sealing bead (15) of the plurality of sealing beads is associated with the front side of the plunger (3) and wherein the rear side serves for connecting to a plunger rod (8), wherein further a front part of the plunger (3) including the front side is covered with a film-like cover layer (18) for otherwise separating the plunger (3) from a medical substance in the use position, wherein the cover layer (18) is configured with different thicknesses, wherein the thickness is greatest in the region of the longitudinal axis (x) and decreased radially outwards from the longitudinal axis (x), wherein a difference between a largest radial dimension (a) of the cover layer (18) and a radial dimension (u) of the cover layer corresponds to a radial dimension (b) that is one fifth or less of the largest radial dimension (a), wherein the radial dimension (u) is the dimension where the thickness of the cover layer becomes less than three times greater than a smallest thickness of the cover layer (18).

2. The plunger (3) according to claim 1, wherein the smallest thickness of the cover layer is from 0.4 to 1 μm.

3. The plunger (3) according to claim 1, wherein the smallest thickness of the cover layer is 0.5 μm.

4. The plunger (3) according to claim 1, wherein the thickness of the cover layer (18) decreases radially outwardly continuously or in steps.

5. The plunger (3) according to claim 1, wherein the smallest thickness of the cover layer (18) is associated with the radially outermost region of the plunger (3) in the region of the first sealing bead (15).

6. The plunger (3) according to claim 1, wherein the cover layer (18) is applied to the plunger (3) in a spray process.

7. The plunger (3) according to claim 1, wherein the cover layer (18) is designed as a separate part (20) and attached to the plunger (3).

8. The plunger (3) according to claim 1, wherein the side of the cover layer (18) facing the plunger (3) has one or more protrusions (21) for form-fitting engagement in corresponding recesses (22) in the front side of the plunger (3).

9. The plunger (3) according to claim 1, wherein a protrusion (21) and an associated recess (22) are arranged symmetrically relative to a longitudinal cross section through the plunger (3) or the longitudinal axis (x) passes through the middle of the protrusion and the associated recess.

10. The plunger (3) according to claim 1, wherein the cover layer (18) has a constant thickness over its entire lateral surface (19) and a different thickness in the region of the first sealing bead (15).

11. The plunger (3) according to claim 10, wherein the constant thickness has a dimension from 0.3 to 3 μm.

12. A plunger (3) for a medical syringe (1), wherein the plunger (3) has a plunger body with a longitudinal axis (x), a lateral surface, a front side, a rear side, and a plurality of sealing beads, wherein a first sealing bead (15) of the plurality of sealing beads is associated with the front side of the plunger (3) and wherein the rear side serves for connecting to a plunger rod (8), wherein further a front part of the plunger (3) including the front side is covered with a film-like cover layer (18) for otherwise separating the plunger (3) from a medical substance in the use position, wherein the cover layer (18) is configured with different thicknesses, wherein the thickness is greatest in the region of the longitudinal axis (x) and decreased radially outwards from the longitudinal axis (x), wherein a side of the cover layer (18) facing the plunger (3) has one or more protrusions (21) for form-fitting engagement in corresponding recesses (22) in the front side of the plunger (3).

13. The plunger (3) according to claim 12, wherein a smallest thickness of the cover layer is from 0.4 to 1 μm.

14. The plunger (3) according to claim 12, wherein a smallest thickness of the cover layer is 0.5 μm.

15. The plunger (3) according to claim 12, wherein the thickness of the cover layer (18) decreases radially outwardly continuously or in steps.

16. The plunger (3) according to claim 12, wherein a smallest thickness of the cover layer (18) is associated with the radially outermost region of the plunger (3) in the region of the first sealing bead (15).

17. The plunger (3) according to claim 12, wherein the cover layer (18) is applied to the plunger (3) in a spray process.

18. The plunger (3) according to claim 12, wherein the cover layer (18) is designed as a separate part (20) and attached to the plunger (3).

19. The plunger (3) according to claim 12, wherein a protrusion (21) and an associated recess (22) are arranged symmetrically relative to a longitudinal cross section through the plunger (3) or the longitudinal axis (x) passes through the middle of the protrusion and the associated recess.

20. The plunger (3) according to claim 12, wherein the cover layer (18) has a constant thickness over its entire lateral surface (19) and a different thickness in the region of the first sealing bead (15).

* * * * *